United States Patent [19]
Senni et al.

[11] 4,326,925
[45] Apr. 27, 1982

[54] PROCESS FOR THE PURIFICATION OF CAPROLACTAME

[75] Inventors: Paolo Senni, Colleferro; Domenico Astarita, Segni-Colleferro, both of Italy

[73] Assignee: SNIA Viscosa Societa' Nazionale Industria Applicazioni Viscosa S.p.A., Milan, Italy

[21] Appl. No.: 122,675

[22] Filed: Feb. 19, 1980

[30] Foreign Application Priority Data

Feb. 28, 1979 [IT] Italy .............................. 20612 A/79

[51] Int. Cl.$^3$ .............................................. B01D 3/34
[52] U.S. Cl. ...................................... 203/37; 203/71; 203/91; 260/239.3 A
[58] Field of Search .................. 260/239.3 A; 203/36, 203/37, 71, 73, 72, 80, 91, 77, 50

[56] References Cited

U.S. PATENT DOCUMENTS

| | | | |
|---|---|---|---|
| 3,156,683 | 11/1964 | Chandler | 260/239.3 A |
| 3,179,657 | 4/1965 | Naglieri | 260/239.3 A |
| 3,904,609 | 9/1975 | Mattone et al. | 260/239.3 A |
| 4,148,793 | 4/1979 | Danziger et al. | 260/239.3 A |

Primary Examiner—Frank Sever
Attorney, Agent, or Firm—Hubbell, Cohen, Stiefel & Gross

[57] ABSTRACT

A process for purifying caprolactame by continuous and/or discontinuous (or batch) vacuum distillation comprises a first stage fast vacuum distillation of the raw caprolactame possibly in the presence of an alkaline and/or alkaline-earth hydroxide, a second stage consisting of a vacuum rectification distillation of the caprolactame obtained in the first stage and a third stage consisting of the fast vacuum distillation of the caprolactame yielded from the second stage, in the presence of an alkaline and/or alkaline-earth hydroxide. The hydroxide amount in the third and possibly the first stage distillation as well varies from 0.05 to 5% preferably from 0.1% to 1%.

13 Claims, No Drawings

PROCESS FOR THE PURIFICATION OF CAPROLACTAME

FIELD OF THE INVENTION

This invention relates to a method of purifying caprolactame, e.g. caprolactame of the same grade as yielded by reacting nitrosyl compounds with carbocyclic derivatives.

BACKGROUND OF THE INVENTION

It is a well known fact that the aforesaid reaction yields, additionally to caprolactame, small amounts of non-cyclic amides, such as acetamide, popionamide, butyramide, n-valeramide, benzamide, tetrahydrobenzamide, hexahydrobenzamide, and moreover, still in small amounts, aliphatic and aromatic cyclocarboxylic acids, epsilon-aminocapronic acid, and unsaturated oxidable substances.

Several methods of purifying caprolactame are known in the art. Thus, for example, when effectuated by reacting nitrosyl compounds with carbocyclic derivatives, the purification of caprolactame (following its extraction from the sulphuric reaction mass and known steps for separating raw caprolactame) is substantially carried out, according to current practice, by means of two separate and discrete chemical treatments, a first one directed to destroying the amides, and a second one directed to reducing or eliminating the easily oxidable substances. More specifically, these treatments consist of subjecting firstly the raw caprolactame to the action of sodium hypochlorite (conversion of the amides into more volatile amines), and subsequently to an oxidizing action, e.g. with potassium permanganate or ozone (decomposition of the oxidable substances); the product, after undergoing that treatment, is subjected to distillations, possibly under vacuum conditions, without rectification, thereby a "polymerization grade" caprolactame is obtained. Said chemical treatments, however, have the following drawbacks:

(1) they are expensive;

(2) they yield impurities of a different nature (such as chloro-lactames, for instance) which, although only some ppm, result in contamination of the caprolactame;

(3) the treatments with hypochlorite-permanganate, respectively hypochlorite-ozone, are not absolutely selective, even when the very high caprolactame-byproducts ratio is taken into account, thereby part of the caprolactame is destroyed by these chemicals, with an attendant appreciable decrease of the yield.

SUMMARY OF THE INVENTION

The Applicant has now surprisingly found a method of purifying caprolactame by the application of only one line of physical purification. With this process, it becomes possible to obtain a caprolactame of a purity even higher than that obtainable with the use of hypochlorite-permanganate, respectively hypochlorite-ozone.

By not applying said treatments of a chemical nature, not only all of the aforesaid disadvantages are eliminated, but a lower cost and improved environmental protection can also be achieved in the purification process.

This invention sets out to provide a caprolactame purification process by vacuum distillation, characterized in that said distillation is carried out, in a continuous and/or discontinuous (batch distillation) manner, in the following stages or steps, in the same order as listed herebelow:

(a) fast vacuum distillation of the raw caprolactame, possibly in the presence of an alkaline and/or alkaline-earth hydroxide;

(b) distillation with vacuum rectification of the caprolactame yielded as distillate from (a), with separation from the high-boiling, and possibly low-boiling byproducts; and (c) fast vacuum distillation of the caprolactame yielded from (b), in the presence of an alkaline and/or alkaline-earth hydroxide.

The term "fast distillation", as used herein, is intended to describe an operation wherein the evaporated material is no more recycled, in any substantial manner, into the evaporation zone. The percentage by weight of the alkaline or alkaline-earth hydroxide, at step (c), and possibly (a) as well, with respect to caprolactame, varies preferably in the 0.05% to 5% range, and more preferably from 0.1% to 1.0%.

DESCRIPTION OF A PREFERRED EMBODIMENT OF THE INVENTION

Advantageously, the temperature of the various steps (a), (b) and (c) are preferably maintained within the following limits:

Step (a)—100° to 150° C.
Step (b)—vapors, 110° to 150° C.; reboiler, 120° to 180° C.;
Step (c)—100° to 150° C.

As the alkaline hydroxide, potassium hydroxide is used of preference, and more preferably sodium hydroxide, whereas when an alkaline-earth hydroxide is used, calcium hydroxide is preferred; however, as the hydroxide, according to this invention, sodium hydroxide is still more preferably employed. Said alkaline or alkaline-earth hydroxides are preferably employed, in accordance with this invention, in the form of a solution, and more preferably of an acqueous solution.

According to a variant of the invention, (mainly suggested by economics and physical-mechanical considerations) the purification of caprolactame is carried out at the steps (a), (b) and (c) such as to obtain:

From Step (a), a distilled portion corresponding to 90–98% by weight with respect to the raw caprolactame, and 2–10% by weight of residue, again with respect to the raw caprolactame;

from Step (b), a head fraction, corresponding to 2–5% by weight with respect to the caprolactame supplied from Step (a), a core fraction, corresponding approximately to 90% by weight of the caprolactame supplied from Step (a), and a residue corresponding to 5–8% by weight again with respect to the caprolactame supplied from Step (a);

from Step (c), a fast distillate to yield a residue corresponding to approximately 5–10% by weight of the caprolactame supplied from Step (b).

In Step (b), the head fraction may or may not be separated from the caprolactame which is supplied to the successive step (c).

The operating conditions which can be adopted for the two fast distillations, as per steps (a) and (c), are the following:

Temperatures in the 125° to 130° C. range;
Residual pressure, 4 mm Hg;
and for the rectification of step (b):
Head temperatures in the 105° to 110° C. range;

Reboiler temperature in the 120° to 165° C. range.

The finally yielded caprolactame has the following characteristics:
Volatile bases, 0.1 meq/kg;
Permanganate Number, 15,000 seconds;
HAZEN color, less than 5;
Absorption at 290 nm, 0.008;
Absorption summation from 260 to 300 nm, 0.290.

None of the individual operations, when carried out separately and/or in a different order from the one provided by the invention, yields caprolactame having the aforesaid characteristics.

A further object of this invention includes the purified caprolactame as obtained with the purification method described hereinabove.

The following example should be considered as merely illustrative and in no way limitative of this invention.

EXAMPLE

Step (a)

Into a glass flask equipped with thermometer, capillary tube for the introduction of nitrogen, vapor collecting and condensing system, vacuum unit, and vacuum measuring gauges, as well as outer electric heater, there are charged 100 parts by weight of raw caprolactame and 0.3 parts by weight of NaOH, as a 50% solution in $H_2O$. The flask is treated up to 110° C. at a residual pressure of 1.2 mm Hg. The results are shown in the following Table 1.

TABLE 1

| CHARGE | 100 parts by weight |
|---|---|
| Total volatile bases charged | 24.3 meq/kg |
| Volatile bases charged as hexahydrobenzamide (HBA) | 17.8 meq/kg |
| Permanganate Number | 0 seconds |
| DISTILLATE | 80 parts by weight |
| Total volatile bases | 10.2 meq/kg |
| HBA volatile bases | 7.4 meq/kg |
| Permanganate Number | 150 seconds |
| TAILS | 20 parts by weight |
| Total volatile bases | 80.7 meq/kg |
| HBA volatile bases | 59.4 meq/kg |
| Permanganate Number | 0 seconds |
| Oligomers | none |

Step (b)

The apparatus utilized to carry out step (b) comprises a glass flask equipped with capillary tube for the introduction of nitrogen, thermometer, pressure gauge for measuring the vacuum, and other electric heater system. Over the flask, there is mounted a 20-plate rectification column which is connected to a reflux head and then to an overall condenser discharging into a distillate collection flask whereto a vacuum is applied. Into the heated flask, are charged 80 parts by weight of the caprolactame from the distillate of step (a); heat is applied after a 3 mm Hg vacuum has been created in the collecting flask (in the boiler the vacuum is of 25 mm Hg). Before the collection is initiated, the caprolactame is fully recycled to ensure that the column operating conditions are achieved. Then, 4 parts by weight of caprolactame are distilled, collected and separated at the head temperature of 124° C., and 64 parts by weight of caprolactame are collected and separated at the temperature of 125° C. Distillation is then discontinued, and in the boiler there remain 12 parts by weight of caprolactame. The results obtained are tabulated in the following Table 2.

TABLE 2

| CHARGE | 80 parts by weight |
|---|---|
| RECTIFICATION HEADS | 4 parts by weight |
| Total volatile bases | 1.78 meq/kg |
| HBA volatile bases | none |
| Permanganate Number | 0 seconds |
| RECTIFICATION TAILS | 12 parts by weight |
| Total volatile bases | 66.5 meq/kg |
| HBA volatile bases | 49.3 meq/kg |
| Permanganate Number | 0 seconds |
| Oligomers | none |
| RECTIFICATION CORE | 64 parts by weight |
| Total volatile bases | 0.17 meq/kg |
| HBA volatile bases | none |
| Permanganate Number | 3800 seconds |

Step (c)

The apparatus employed to carry out this step is the same as for step (a). There are charged into it 64 parts by weight of caprolactame from the rectification core (step (b)) and 0.15 parts by weight of NaOH as a 50% solution in $H_2O$. One proceeds as in step (a), and the results are tabulated in the following Table 3.

TABLE 3

| CHARGE | 64 parts by weight |
|---|---|
| TAILS | 6.4 parts by weight |
| Total volatile bases | 0.76 meq/kg |
| Permanganate Number | 0 seconds |
| Oligomers | none |
| DISTILLATE | 57.6 parts by weight |
| Total volatile bases | 0.04 meq/kg |
| HBA volatile bases | none |
| Permanganate Number | 15,000 |
| Absorption at 290 nm | 0.008 |

We claim:
1. A process of purifying raw caprolactame by vacuum distillation, wherein said distillation is carried out, in either a continuous or discontinuous manner, in the following steps and in the order listed herebelow:
  (a) feeding said raw caprolactame to a fast vacuum distillation, said fast vacuum distillation yielding a caprolactame containing distillate;
  (b) feeding all of the distillate from step (a) directly to a distillation with vacuum rectification, with separation from the high-boiling, and possibly low-boiling by-product;
  (c) feeding said caprolactame yielded from step (b) to a fast distillation which is carried out in the presence of a compound selected from the group consisting of an alkaline hydroxide and an alkaline-earth hydroxide, said fast vacuum distillation yielding a purified caprolactame containing distillate; and
  (d) withdrawing all of the distillate of step (c) as product.

2. A process according to claim 1, wherein the percentage by weight of said compound with respect to said caprolactame in step (c) varies from about 0.05% to about 5%.

3. A process according to either claim 1 or 2, wherein the temperatures of steps (a), (b) and (c) are maintained within the following limits:
  step (a)—100° to 150° C.;
  step (b), vapors—110° to 150° C., reboiler—120° to 180° C.;

step (c)—100° to 150° C.

4. A process according to any of claims 1 or 2 wherein hydroxide is used as said alkaline hydroxide.

5. A process according to claim 4, characterized in that said sodium hydroxide is used in the form of an acqueous solution.

6. A process according to any of claims 1 or 2 wherein said purification of said raw caprolactame is carried out in steps (a), (b) and (c) such as to obtain:
   from step (a), a distillate portion corresponding to 90-98% by weight with respect to said raw caprolactame, and 2-10% by weight of residue, with respect to said raw caprolactame;
   from step (b), a head fraction corresponding to 2-5% by weight with respect to said caprolactame supplied from step (a), a core fraction corresponding to approximately 90% by weight of said caprolactame supplied from step (a), and a residue corresponding to 5-8% by weight with respect to said caprolactame supplied to step (a), and from step (c), a fast distillate yielding a residue corresponding to approximately 5-10% by weight of said caprolactame supplied from step (b).

7. A process according to claim 2, wherein said percentage varies from about 0.1% to about 1%.

8. Purified caprolactame as obtained by the process according to either of claim 1.

9. A process according to claim 1, wherein step (a) is carried out in the presence of a compound selected from the group consisting of an alkaline hydroxide and an alkaline-earth hydroxide.

10. A process according to claim 9, wherein the percentage by weight of said compound with respect to said caprolactame in step (a) varies in each case from about 0.05% to about 5%.

11. A process according to claim 10, wherein said percentage varies from about 0.1% to about 1%.

12. A process according to claim 1, wherein said caprolactame is produced by the lactamization of hexahydrobenzoic acid and contains impurities such as hexahydrobenzamide in substantial amounts prior to purification.

13. A process according to claim 1, wherein step (b) yields a caprolactame containing core fraction which is fed to the fast distillation of step (c).

* * * * *